United States Patent [19]

Teed

[11] Patent Number: 4,645,501
[45] Date of Patent: Feb. 24, 1987

[54] DISPOSABLE ABSORBENT GARMENT CONSTRUCTION

[75] Inventor: Richard K. Teed, Greenwood, S.C.

[73] Assignee: Professional Medical Products, Inc., Greenwood, S.C.

[21] Appl. No.: 613,242

[22] Filed: May 24, 1984

[51] Int. Cl.⁴ ............................................. A61F 13/16
[52] U.S. Cl. ................................................... 604/390
[58] Field of Search ............... 604/385 R, 390, 389, 604/386, 366; 428/500

[56] References Cited

U.S. PATENT DOCUMENTS

| | | | |
|---|---|---|---|
| 2,834,347 | 5/1958 | Connally | 604/389 |
| 3,484,835 | 12/1969 | Trounstine et al. | 264/284 |
| 3,554,195 | 1/1971 | Murdoch | 604/365 |
| 3,630,201 | 12/1971 | Endres | 604/390 |
| 3,642,001 | 2/1972 | Sabee | 604/390 |
| 3,853,129 | 12/1974 | Kozak | 604/390 |
| 3,860,003 | 1/1975 | Buell | 604/385 R |
| 3,867,940 | 2/1975 | Mesek | 604/366 |
| 3,881,488 | 5/1975 | Delanty et al. | 604/374 |
| 3,948,267 | 4/1976 | Karami | 604/390 |
| 3,967,624 | 7/1976 | Milnamow | 604/390 |
| 4,050,462 | 9/1977 | Woon et al. | 604/365 |
| 4,063,559 | 1/1977 | Tritsch | 604/390 |
| 4,069,822 | 1/1978 | Buell | 604/366 |
| 4,081,301 | 3/1978 | Buell | 156/164 |
| 4,177,812 | 12/1979 | Brown et al. | 604/390 |
| 4,210,144 | 6/1980 | Sarge, III et al. | 604/390 |
| 4,253,461 | 3/1981 | Strickland et al. | 604/389 |
| 4,327,730 | 5/1982 | Sorensen | 604/385 R |

Primary Examiner—John D. Yasko
Attorney, Agent, or Firm—Luke J. Wilburn, Jr.

[57] ABSTRACT

An improved disposable absorbent garment having opposed sides and ends to be located respectively between the legs and about the waist of a wearer, and having an inner moisture-absorbent layer with an outer water-impervious plastic sheet secured thereto. Fastener tabs attached to opposite sides of the garment adjacent the ends of the same have adhesively coated end portions for pressure attachment to the outer surface of the plastic sheet to secure the garment about the waist of the wearer. The outer surface of the plastic sheet is patterned with two sets of spaced parallel continuous raised ridges respectively extending parallel and perpendicular to the end edges of the garment to form a generally rectangular surface pattern, and the tabs are located so that their adhesively coated end portions extend generally parallel and perpendicular to the sets of ridges when attached to the outer surface of the plastic sheet, thereby enabling the tabs to be peeled from and adhesively reattached and repositioned a number of times on the garment for adjustment of the garment on the wearer without damage to the plastic outer sheet.

6 Claims, 7 Drawing Figures

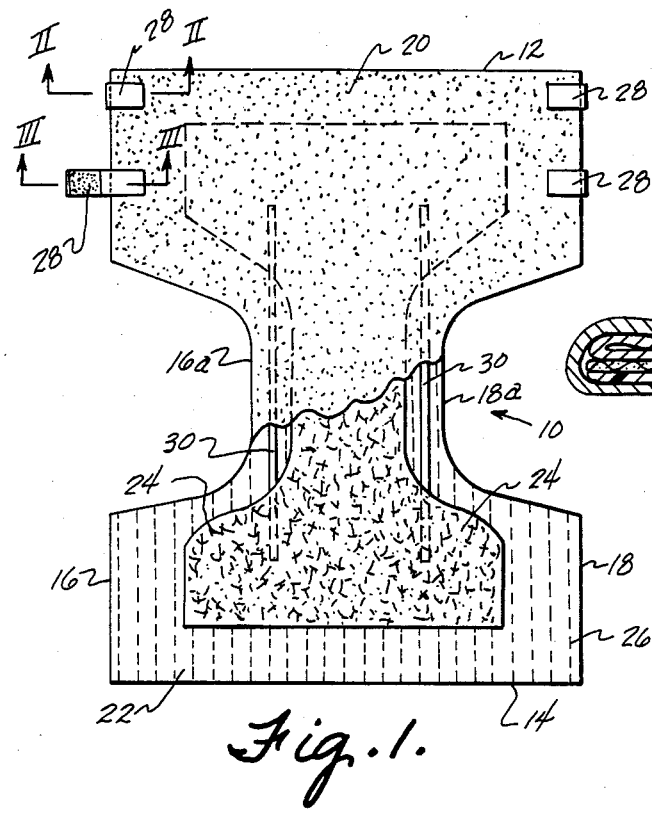
Fig. 1.
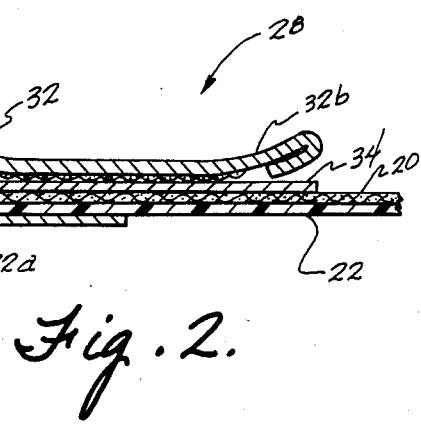
Fig. 2.
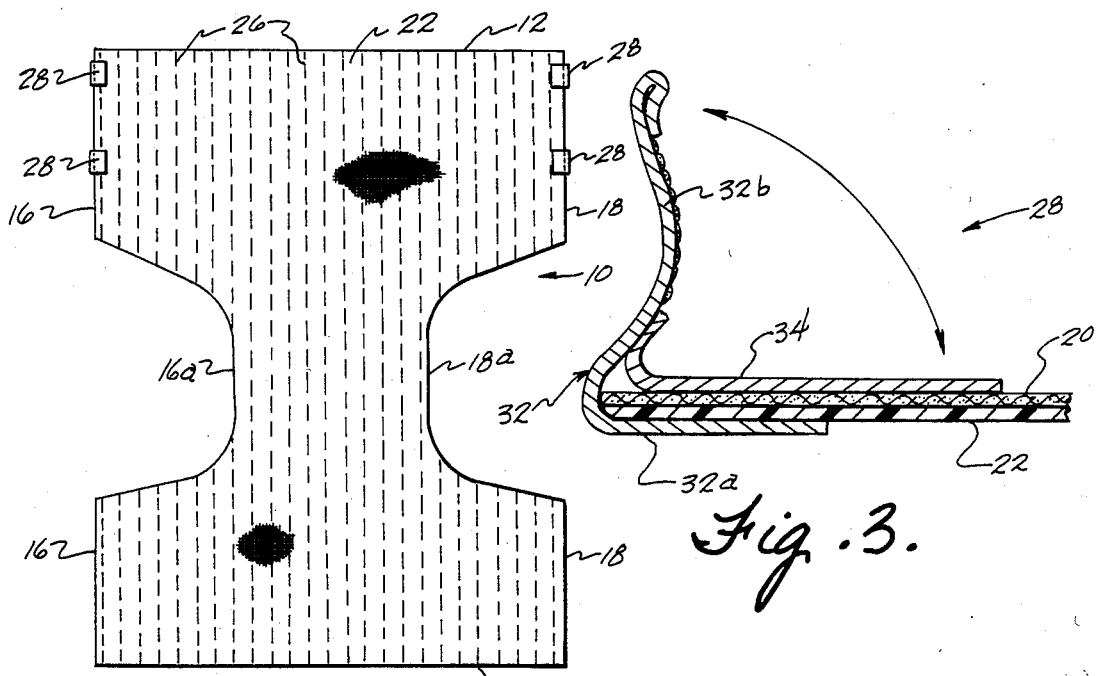
Fig. 3.
Fig. 4.

DISPOSABLE ABSORBENT GARMENT CONSTRUCTION

This invention relates to an improved disposable absorbent garment, and, more particularly, to a disposable absorbent garment of the diaper type having adhesively coated fastener tabs which are repositionable on the garment to permit removal, replacement, and adjustment of the garment on the waist and torso of a wearer.

BACKGROUND OF THE INVENTION

Disposable absorbent garments, such as diapers, are well known and are widely used for infants and incontinent adults to absorb waste discharges from the human body and retain the same until the garment is discarded. Such disposable incontinent briefs and diapers generally are composed of an inner moisture absorbent batt or layer of material with an outer water-impervious thin plastic sheet suitably secured thereto. The garment has opposed elongate sides which may or may not be contoured and which are located to reside in the crotch area of the wearer, and opposed ends which overlie and surround the waist of the wearer.

To enhance the aesthetic appearance and reduce surface tackiness of the outer plastic sheet of the diaper, the sheet is generally embossed with a surface pattern to simulate the appearance of a woven fabric. Generally the outer surface pattern of the sheet is a raised diamond or square pattern running lengthwise between the ends of the diaper and separated by recessed channels or grooves. One such embossed plastic sheet or film construction is disclosed in U.S. Pat. No. 3,484,835.

The opposite ends of the diaper are generally secured to each other about the wearer's waist by adhesively coated fastener tabs. One or two such fastener tabs generally are provided along opposite side edges of one end of the diaper and have adhesively coated end portions which are manually released from the tab structure and secured by pressure to the outer surface of the plastic sheet at the other end of the diaper to secure the two ends about the wearer's waist.

At times, it is desirable to unfasten and reposition the fastener tabs of the disposable garment, as when the garment is used as a training diaper, or when the initial securement of the garment about the waist is too tight or too loose. In such cases, the ends of the adhesive fastener tabs must be peeled from the outer surface of the plastic sheet and subsequently adhesively reattach to the sheet when the garment is adjusted. Because of the need for a strong bond of the fastener tab adhesive to the plastic sheet to ensure positive securement of the garment on the body of the wearer, the fastener tab cannot generally be removed from the surface of the plastic sheet without tearing and pulling away the thin water-impervious plastic outer cover of the garment.

In an effort to provide a releasable and refastenable fastener tab, disposable garment fastener tabs more recently have been constructed with an additional short, intermediate plastic reinforcing strip which has a non-adhesive face attached to the adhesive end portion of the fastener tab, and an inner adhesively coated face for direct securement to the thin plastic sheet of the diaper. Upon initial securement of the freed end of the tab to the plastic sheet of the garment, the intermediate plastic reinforcing strip adhesively attaches by pressure directly to the outer surface of the plastic sheet. When it is desired to release the end of the fastener tab from the garment, it is pulled from the surface of the reinforcing strip which stays attached to and reinforces the thin plastic sheet. When the adhesive end portion of the tab is to be reattached to the surface of the plastic sheet, it must be directly repositioned on the reinforcing plastic strip, otherwise the end of the tab can not be removed again from the plastic sheet without tearing the sheet. Although this modified fastener tab construction does permit removal and reattachment of the tab to the outer plastic sheet of the garment, it does not permit repeated repositioning of the tab at other locations on the garment to adjust the same on the wearer.

BRIEF OBJECTS OF THE PRESENT INVENTION

It is therefore an object of the present invention to provide an improved disposable absorbent garment of the diaper type having adhesively coated fastener tabs which may be readily attached, removed, and repositioned at various locations on the outer surface of the garment to adjust the same without tearing or damaging the plastic outer sheet of the garment.

It is another object to provide an improved disposable moisture absorbent garment construction having adhesive fastener tabs for securing the same about the body of the wearer and wherein the tabs may be quickly and easily repositioned at various locations on the garment outer surface to remove and readjust the same on the wearer.

It is a further object to provide an improved disposable absorbent garment having adhesively coated fastener tabs of simplified construction which may be released and repositioned repeatedly on the outer plastic surface of the garment during the use of the same without damage to or destruction of the garment.

BRIEF DESCRIPTION OF THE DRAWINGS

The above as well as other objects of the present invention will become more apparent, and the invention will be better understood, from a detailed description of the same, when taken together with the accompanying drawings, in which:

FIG. 1 is a plan view of the inside surface of a disposable moisture absorbent garment, or diaper, incorporating features of the present invention, with the diaper in an extended, flat condition and with portions of the inside surface broken away to better show the construction of the diaper;

FIG. 2 is an enlarged cross-sectional view of a portion of the diaper of FIG. 1, taken along line II—II thereof and looking in the direction of the arrows;

FIG. 3 is an enlarged cross-sectional view of a portion of the diaper of FIG. 1 taken along line III—III thereof and looking in the direction of the arrows;

FIG. 4 is a plan view of the outside surface of the diaper of FIG. 1, showing a portion of the surface pattern of the plastic outer sheet of the same.

FIG. 7 is a view of the diaper of FIG. 1 showing the manner in which the ends of the same are folded, disposed, and secured together by the fastener tabs of the

BRIEF SUMMARY OF THE INVENTION

Figure 5:
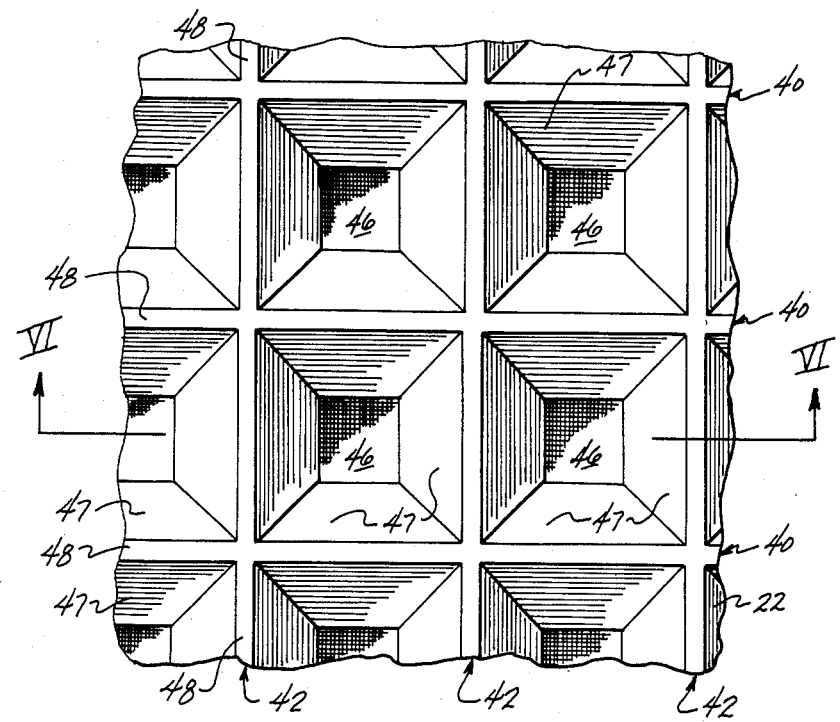
FIG. 5 is a greatly enlarged plan view of a small portion of the outer surface of the diaper of FIG. 4, showing in more detail the pattern appearing on the surface thereof.

The present invention comprises an improved disposable absorbent garment, such as a diaper, having opposed sides and ends to be located respectively between the legs and about the waist of the wearer, and having an inner moisture absorbent layer with an outer water-impervious plastic sheet secured thereto. Fastner tabs attached to opposed side edges of the garment adjacent one end of the same are employed to secure the ends of the garment about the waist of the wearer. The outer surface of the plastic water-impervious sheet of the garment has two sets of spaced parallel continuous raised ridges running respectively parallel and perpendicular to the end edges of the garment to form a generally rectangular surface pattern. The fastner tabs are located on the garment so that their adhesively coated end portions extend generally parallel and perpendicular to the respective sets of ridges when attached to the outer surface of the plastic sheet. The arrangement of the surface pattern permits the adhesively coated tab end portions to be readily peeled from the surface of the sheet and subsequently repositioned in other locations thereon to adjust the garment on the wearer.

DETAILED DESCRIPTION OF THE PREFERRED EMBODIMENTS

Referring more particularly to the drawings, FIG. 1 is a plan view of the inside surface of a disposable absorbent garment, or diaper 10, which may be of variable sizes so as to be worn by human infants or adults to absorb and contain body wastes. As shown, diaper 10 has opposed ends having parallel end edges 12, 14, and opposed sides 16, 18 the mid-portions 16a, 18a of which are shown to be contoured inwardly to more closely conform to the crotch and inner thigh portions of the body of a wearer. As shown in FIGS. 1 and 4, diaper 10 is in a flat extended configuration, and includes a thin inner sheet 20 of non-woven water-pervious material, such as a polyester non-woven fabric, and an outer thin water-impervious plastic film or sheet 22, such as a polyethylene film. Disposed between the inner and outer sheets is a non-woven batt 24 of highly water absorbent material, such as wood pulp or cellulose, which may be wrapped in thin tissue to contain the same. The sheets 20, 22 and batt 24 of the diaper are secured together in conventional manner by lines 26 of adhesive material to form a unitary structure, and opposite side edges at one end 12 of the diaper are provided with adhesive fastner tabs 28 for securement to the opposite end 14 of the diaper when the diaper is located about the waist of a wearer. See FIG. 7.

Figure 7:
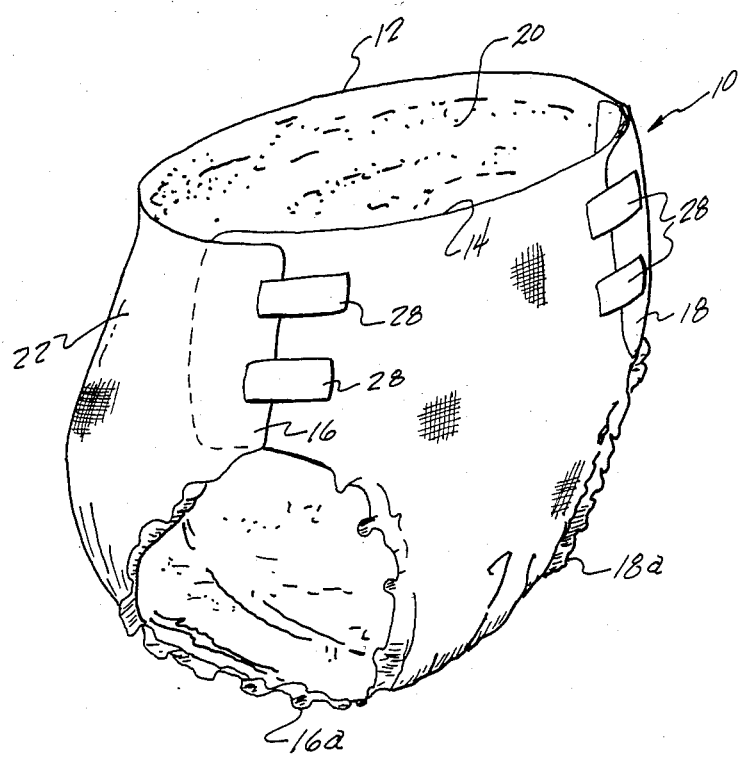

The interior of the diaper construction conventionally may be provided with elastic strips 30 which extend generally parallel to the side edges of the diaper in the contoured crotch area to gather and more closely conform the contoured central portions of the crotch area of the diaper to the inner thigh portions of the wearer, as seen in FIG. 7.

As best shown in FIGS. 2 and 3, the adhesive tabs 28 of the diaper are formed of a paper outer tab portion 32, one end 32a of which is adhesively fixed to an outer edge surface of the water-impervious plastic sheet 22, and the other end 32b of which has an adhesively coated inner face which is removably secured to the smooth outer surface of a plastic inner tab portion 34. Tab portion 34 is adhesively fixed to the inner surface of non-woven inner sheet 20.

To use tabs 28 to secure the ends 12, 14 of the diaper about the waist of a wearer, the adhesively coated end 32b of each tab is peeled and released from the inner tab portion 34 and lifted, as seen in FIG. 3, to be reapplied by pressure to the outer surface of plastic sheet 22 at the other end 14 of the diaper when the diaper ends are placed about the waist of the wearer, as shown in FIG. 7. Note the position of the tab end 32b before its release from the inner portion 34 of the tab, as shown in FIG. 2, and after its release and prior to its attachment to the outer surface of the other end of the diaper, as shown in FIG. 3.

The foregoing description of the diaper construction shown in FIGS. 1–4 describes a conventional diaper of the prior art which does not normally permit release and repositioning of the ends of the fastener tabs 28 after once being secured to the plastic sheet 22 in position of wear. Such a diaper construction typically is produced in a continuous manufacturing operation wherein continuous lengths of the outer and inner sheets 20, 22 are fed in longitudinal direction and combined with the water absorbant batt, elastic strips, and fastner tabs, with subsequent separation of the individual diapers by cutting along their end edges. Such diaper constructions and various methods of manufacture are well known to those skilled in the art and certain are described in U.S. Pat. Nos. 4,081,301; 4,050,462; and 3,881,488.

Heretofore, such diaper constructions, as described, have not been capable of adjustment on the wearer by repositioning the adhesive coated tabs at various locations on the outer surface of the plastic outer sheet of the diaper. Because of the thinness of the plastic outer sheet, e.g., 1 to 2 mils in thickness, and the necessary adhesive bonding of the tab to ensure retention of the diaper on the wearer, attempts to disattach the adhesive-coated ends 32b of the tabs from the outer surface of the plastic sheet 22 resulted in a tearing away of the plastic sheet.

Figure 6:
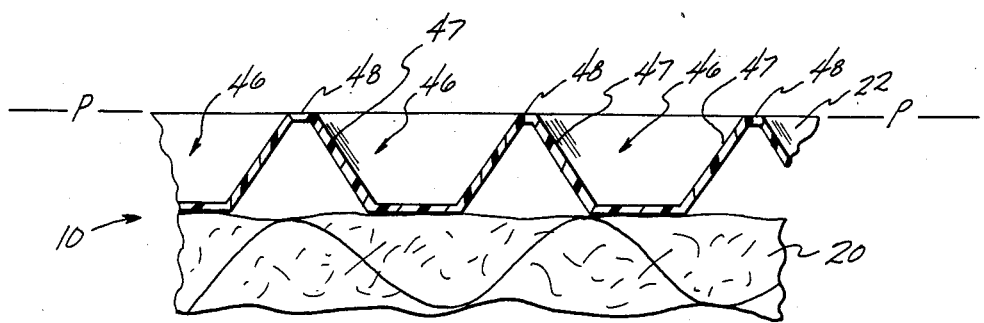
FIG. 6 is a cross-sectional view taken along line VI—VI of FIG. 5 and looking in the direction of the arrows.

FIGS. 4–6 illustrate, in detail, the embodiments of the present invention which permit repeated reattachment and repositioning of adhesive coated fastener tabs to the outer surface of the outer plastic sheet of the diaper without tearing the sheet or loss of utility of the diaper. As best seen in FIGS. 4–6, the outer surface of water impervious plastic sheet 22 of diaper 10 is provided with a patterned configuration, as in an embossing operation. The surface pattern comprises two sets of a plurality of continuous spaced raised ribs or ridges, one set 40 of which extends parallel to the end edges of the diaper, and the other set 42 of which extends perpendicular thereto. Note FIGS. 5 and 6. The ridges or ribs are separated by generally square recessed surface portions 46 having downwardly tapering sides 47 to define a generally square pattern of raised ridges extending in lengthwise and widthwise direction of the diaper.

As seen in FIGS. 1 and 7, the adhesive coated ends 32b of fastener tabs 28 are thus disposed to be applied by pressure to the patterned ribbed outer surface of plastic sheet 22 with the length of the tab ends running parallel and perpendicular to the respective sets of raised ridges 40, 42, and in adhesive securement to the upper flat surfaces 48 of the ridges. By providing a surface pattern of continuous ridges 40, 42 on the outer surface of plastic sheet 22 with the ridges disposed to receive the adhesive coated ends 32b of the fastener tabs 28 in parallel and perpendicular directions therewith, it has been discovered that the ends of the tabs may be peeled from and repositioned at various locations on the plastic sheet without tearing the sheet, and while retaining the necessary adhesion to ensure securement of the diaper on the body of the wearer.

It has been found that best results in adhesive securement with repositionability of the adhesive fastener tabs is obtained when the total upper surface area 48 of the ridges 40, 42 comprises less than about 20% of the total surface area of the sheet, that is, when the recessed surface portions of the sheet below the plane P of the ridge surfaces as seen in FIG. 6, comprise about 80% or more of the total surface area of the sheet. With such a patterned configuration and arrangement of the pattern parallel and perpendicular to tab peel direction, sufficient surface area of sheet 22 is provided for contact by the adhesive tab to ensure positive securement of the diaper on the wearer while permitting the tab to be peeled from the diaper and repositioned at various locations thereon. As seen in FIG. 7, the length of the end of the tabs, in use, are disposed parallel and perpendicular to the two sets of the ridges which extend parallel and perpendicular to the end edges of the diaper.

The invention may be illustrated by specific examples of preferred surface patterns for the outer surface of plastic sheet 22 of the diaper, as follows:

EXAMPLE I

A continous length of a one mil thick polyethelene sheet is embossed by a heated calender embossing roll to form a surface pattern of two sets of continuous parallel ridges having upper surfaces 48 (as illustrated in FIGS. 5 and 6) of 0.0004 inch width extending parallel and perpendicular to the longitudinal direction of the sheet. The ridges are separated by recessed square portions 46 of 0.0055 inch square and having a recessed depth of 0.0023 inch. The plastic sheet 22 is thus provided with a total upper ridged surface area 46 of approximately 13% of the total patterned surface area of the sheet.

The thus patterned continous sheet of plastic film is combined on appropriate processing machinery with other components to form diaper constructions as shown in FIGS. 1 and 4, with the continuous ridges 42, 44 of the sheet extending parallel and perpendicular to the end and side edges of the diaper, i.e., forming a square pattern in machine path direction, and with the raised ridges forming the outer surface of the diaper. Fastener tabs of the construction shown in FIGS. 2 and 3 are then tested for adhesion to the outer surface of the plastic sheet of the diaper by the followdng procedure:

A number of fastener tabs secured to diaper constructions as shown in FIGS. 1 and 4 are removed from the side edges of the ends of the diapers by cutting with scissors. The tabs are maintained intact, with the adhesive ends 32b thereof secured to the intermediate release strip 34 of the tab. A corresponding number of strips of the diaper polyethylene film 22 with non-woven sheet 20 adhesively secured thereto are cut from the opposite ends of the diapers from which the tabs were removed. These strips of non-woven-backed polyethylene film are approximately six inches long and slightly wider than the fastner tabs. The adhesively coated end of each fastner tab was released from its intermediate release strip and applied by pressure to the outer surface of an embossed plastic sheet strips, with the lengthwise direction of the tab extending parallel and perpendicular to the surface of the raised ridges of the sheet. Controlled pressure application of the adhesive tab to the ridged surfaces of the strip was obtained by utilizing a 4½ pound mechanically operated rubber covered roller approved by The Pressure Sensitive Tape Council. The mechanically operated roller was passed over the tab and sheet strip once in each lengthwise direction of the tab. Specimens of the thus combined tabs and plastic sheets of the diaper constructions were tested within one minute after pressure adhesion of each.

The specimens were tested in an Instron Tensile Tester, Model 1122, utilizing a crosshead speed of 12 inches per minute and a gage length of 1.5 inches. The end of each tape tab was placed in the top grip of the Instron tester and the end of the polyethylene film strip in the bottom grip of the tester so that a minimum amount of slack was in the combined tab and plastic sheet. Using a finger to support the tape and film so that a 90 degree peel is effected when the crosshead is set in motion, the crosshead was activated and readings taken between preset points of peel from 0.5 inches to 1.5 inches of separation. Load values of peel displayed on a recorder were recorded in grams per tab width. Fifteen specimens tested had an average peel load of 560 grams per tab width to peel the tab from the sheet surface. The tapes so peeled could be adhesively peeled and repositioned repeatedly on the plastic sheet surface without tearing the sheet and without significant loss in strength of bond between the tab and sheet.

Another set of fastener tabs and plastic strip specimens prepared from diapers constructed as set forth above were tested on the Instron Tester, except that in each test, the adhesive ends of the fastner tabs were applied to the surface of the plastic sheet in a peel direction diagonal to the raised surface ridges, i.e., such that the length of the fastener tabs extended at a 45 degree angle to the longitudinal directions of the raised ridges of the sheet. Fifteen specimens were tested as above described with an average peel load of 646 grams per tab width. In six of the fifteen specimens tested, peeling of the fastner tab from the plastic sheet in the Instron Tester caused tearing of the plastic sheet.

The foregoing comparison indicates that it is necessary that the raised ridge pattern on the outer surface of the embossed plastic sheet of the diaper be located in a square pattern, in machine manufacture direction, i.e., parallel to the ends and sides of the diaper, so that the fastener tab is applied and peeled in a direction parallel and perpendicular to the patterned ridge surface of the sheet.

EXAMPLE II

A number of diapers were manufactured and constructed as in Example I, except that the embossed pattern on the outer surface of the plastic sheet of the diaper had ridge surfaces of 0.00059 inch width, a recessed portion of 0.018 inch square, and a recessed surface depth of 0.0095 inch to provide a raised ridge surface area comprising approximately 7 percent of the total surface area of the embossed plastic sheet.

Fifteen specimen samples of tabs and plastic sheet strips were cut, prepared and tested as in Example I utilizing a tab adhesion and peel direction parallel and perpendicular to the pattern ridges. Other specimen samples were prepared and tested as in Example I and exhibited an average peel load of 405 grams per tab width.

Other specimen samples were prepared and tested as in Example I with application of the tabs in a diagonal direction to the parallel ridges and exhibited an average peel load of 405 grams per tab width.

Although the peel tests for the diagonal peel direction tab positions did not result in a tearing of the plastic sheet, as in Example I, the low adhesion peel load value of 405 grams indicates a significant lowering in adhesion of the tab to the sheet, reducing the chances of positive resecurement of the diaper on the body of the wearer.

It is contemplated that various materials may be employed as the adhesive for the fastener tabs of the present invention. Particularly good results have been obtained in the use of a polyethylene-based hot melt pressure sensitive adhesive manufactured by Shell Chemical Company under the name "Kryton".

The diaper may be constructed of various types of plastic film, non-woven sheet, and moisture absorbent batt materials. Typically the water-impervious outer film may be a 1 mil film embossed to approximately a 2 mil thickness or height and backed with a 2 mil thick non-woven polyester sheet. The fastner tabs may be composed of an outer paper tape of 6 mils thickness having a 5 mil thick intermediate plastic release tape for securement of the adhesive-coated end of the paper tape prior to its attachment to the plastic sheet of the diaper.

Diapers prepared in accordance with the present invention when applied to the body of a wearer can be repeatedly adjusted and the tabs repositioned thereon without tearing the plastic sheet and without noticable loss of retention of the tabs on the diaper surface.

That which is claimed is:

1. An improved disposable absorbent garment having opposed sides and ends to be located respectively between the legs and about the waist of a wearer, an inner moisture absorbent layer and an outer water-impervious unitary plastic sheet secured thereto, fastener tabs attached to opposite sides of the garment adjacent an end of the same, each tab having an adhesively coated end portion for pressure attachment to the outer surface of the plastic sheet to secure the garment about the waist of the wearer, the outer surface of the unitary plastic sheet defining two sets of spaced parallel continous raised ridges respectively extending generally parallel and perpendicular to the end edges of the garment to form a generally rectangular surface pattern therein, said tabs being located on the garment so that their adhesively coated end portions extend generally parallel and perpendicular to the respective sets of ridges when attached to the outer surface of the plastic sheet, and said ridges defining a raised surface area of the sheet for contact with said adhesively coated end portions of the tabs to secure the same thereto during garment use while permitting the tab end portions to be readily peeled from the surface of the plastic sheet without damage thereto for subsequent adhesive repositioning of the same on the sheet.

2. A garment as defined in claim 1 wherein said ridges on the outer surface of the plastic sheet are separated by recessed surface portions of the sheet.

3. A garment as defined in claim 2 wherein the total raised surface area of the ridges of the sheet comprises less than about twenty percent of the total patterned surface area of the plastic sheet.

4. A garment as defined in claim 3 wherein the raised surface area of the ridges comprises between about seven to thirteen percent of the patterned surface area of the plastic sheet.

5. A garment as defined in claim 3 wherein the plastic sheet has a thickness of between about 1 to 2 mils.

6. A garment as defined in claim 1 wherein the plastic sheet is embossed to define said sets of spaced parallel continuous raised ridges.

* * * * *